United States Patent [19]

Dewhirst

[11] 4,244,970

[45] Jan. 13, 1981

[54] METHOD OF TREATING INFLAMMATION

[75] Inventor: Floyd E. Dewhirst, Cambridge, Mass.

[73] Assignee: Forsyth Dental Infirmary for Children, Boston, Mass.

[21] Appl. No.: 105,717

[22] Filed: Dec. 20, 1979

[51] Int. Cl.³ .......................................... A61K 31/12
[52] U.S. Cl. ................................................ 424/331
[58] Field of Search ...................................... 424/331

[56] References Cited

U.S. PATENT DOCUMENTS

| | | | |
|---|---|---|---|
| 3,989,275 | 8/1975 | Houlihan | 424/331 |
| 3,924,002 | 12/1975 | Duennenberger et al. | 424/331 |
| 4,038,415 | 7/1977 | Rajadhyaksha et al. | 424/331 |

*Primary Examiner*—Stanley J. Friedman
*Attorney, Agent, or Firm*—Richard P. Crowley

[57] ABSTRACT

A method of treating inflammation and inhibiting prostaglandin synthesis employing 2-hydroxybenzophenone and substituted 2-hydroxybenzophenones.

20 Claims, No Drawings

METHOD OF TREATING INFLAMMATION

BACKGROUND OF THE INVENTION

Various nonsteroidal compositions, such as aspirin, phenylbutazone, indomethacin and other nonsteroidal compounds, and well as steroid compounds, such as adrenocorticosteroids, have been suggested and used as anti-inflammatory agents.

It is desirable to provide new and useful anti-inflammatory agents and prostaglandin synthetase inhibitors which are nonsteroid in nature and which avoid the disadvantages of the prior art nonsteroid and steroid compositions.

SUMMARY OF THE INVENTION

My invention relates to the treatment of inflammation and the inhibition of prostaglandin synthesis by the use of 2-hydroxybenzophenone and substituted 2-hydroxybenzophenone compounds and to novel anti-inflammatory compositions containing, as active ingredients, 2-hydroxybenzophenone and certain substituted 2-hydroxybenzophenone compounds.

It has been discovered that 2-hydroxybenzophenone and the substituted 2-hydroxybenzophenone compounds of this invention act as medicinal agents which inhibit the synthesis of prostaglandins and are useful as topical and systemic anti-inflammatory agents. Certain of my compounds are novel, while other, while not novel, have not been used or suggested for use as inhibitors of prostaglandin synthesis or as anti-inflammatory agents.

My invention is directed to the use of known and novel 2-hydroxybenzophenones as inhibitors of prostaglandin synthesis and as anti-inflammatory agents. The compounds of my invention can be represented generally by the structural formula:

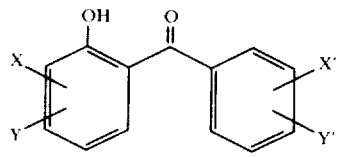

where X, Y, X', and Y' represent hydrogen or halogen, such as chloro, fluoro, bromo, or iodo radicals, lower alkyl radicals, such as $C_1$-$C_8$ radicals, such as methyl, ethyl, propyl and butyl, lower haloalkyl radicals, such as trifluoro, trichloro or tribromo methyl radicals, and lower alkoxy radicals, such as $C_1$-$C_8$ radicals such as methoxy, ethoxy, propoxy, and octyloxy radicals or combinations thereof and the salts thereof.

In particular, my invention concerns those preferred compounds where X and Y are substituents in the 4 and 5 positions and X' and Y' are substituents in the 2', 3', 4', and 6' positions. Representative compounds include but are not limited to those having the following structures:
(1) 2-hydroxybenzophenone
(2) 2-hydroxy-4-methoxybenzophenone
(3) 4'-chloro-2-hydroxy-4-methoxybenzophenone
(4) 2', 3'-dichloro-2-hydroxy-4-methoxybenzophenone
(5) 2', 6'-dichloro-2-hydroxy-4-methoxybenzophenone
(6) 3'-chloro-2-hydroxy-4-methoxy-2'-methylbenzophenone
(7) 2-hydroxy-4-methoxy-3'-trifluoromethylbenzophenone
(8) 2-hydroxy-4'-methyl-4-methoxy-benzophenone
(9) 2-hydroxy-4-octyloxybenzophenone
(10) 5-chloro-2-hydroxy-4-methylbenzophenone
(11) 5-chloro-2-hydroxybenzophenone
(12) 4'-chloro-2-hydroxybenzophenone
(13) 2-hydroxy-5-methylbenzophenone
(14) 2',3'-dichloro-2-hydroxy-5-methylbenzophenone
(15) 2',6'-dichloro-2-hydroxy-5-methylbenzophenone
(16) 3'-chloro-2',5-dimethyl-2-hydroxybenzophenone
(17) 2-hydroxy-5-methyl-3'-trifluoromethylbenzophenone and other compounds and the salts thereof. The structure of these compounds is shown in Table I. Compounds 1-3 and 8-13 are known and commercially available. They have been described in the patent literature for use as UV absorbers and stabilizers for plastics. See U.S. Pat. Nos. 2,773,903, 2,861,104, 3,073,866, and 3,098,842. Compounds 2 and 9 are used medicinally in sunscreen preparations (see Cutting's Handbook of Pharmacology, T. Z. Csaky, Appleton-Century-Crofts, New York, 1979).

My compounds may be employed alone or preferably in pharmaceutical nontoxic carrier materials in either liquid or solid form, that is a solution, dispersion, suspension, emulsion or lotion, such as in oil, alcohols glycols, glycerine, starch, talc, sucrose and the like. My compounds may be employed as active anti-inflammatory agents alone or in combination or with other agents, as well as in combination with those additive and supplemental materials typically employed and used in pharmaceutical compositions.

TABLE I

Preferred compounds

| | 4 | 5 | 2' | 3' | 4' | 6' |
|---|---|---|---|---|---|---|
| 1 | —H | —H | —H | —H | —H | —H |
| 2 | —OCH₃ | — | — | — | — | — |
| 3 | —OCH₃ | — | — | — | —Cl | — |
| 4 | —OCH₃ | — | —Cl | —Cl | — | — |
| 5 | —OCH₃ | — | —Cl | — | — | —Cl |
| 6 | —OCH₃ | — | —CH₃ | —Cl | — | — |
| 7 | —OCH₃ | — | — | —CF₃ | — | — |
| 8 | —OCH₃ | — | — | — | —CH₃ | — |
| 9 | —OC₈H₁₇ | — | — | — | — | — |
| 10 | —CH₃ | —Cl | — | — | — | — |
| 11 | — | —Cl | — | — | — | — |
| 12 | — | — | — | — | —Cl | — |
| 13 | — | —CH₃ | — | — | — | — |
| 14 | — | —CH₃ | —Cl | —Cl | — | — |
| 15 | — | —CH₃ | —Cl | — | — | —Cl |
| 16 | — | —CH₃ | —CH₃ | —Cl | — | — |
| 17 | — | —CH₃ | — | —CF₃ | — | — |

My compounds are used in the treatment of conditions in mammals (human and animal) exhibiting pain, fever and inflammation, or conditions involving the synthesis of prostaglandins. The compounds may be administered in a variety of ways, but typically are employed in the area of pain or inflammation by topical application in a lotion, powder, solution or other form or by systemic administration in any appropriate pharmacological preparation.

A therapeutic amount of the 2-hydroxybenzophone should be employed to reduce inflammation, which may range, for example, from a single to multiple treatments, such as 0.1 mg to 100 mg per kg of body weight per day, for example 1 mg to 25 mg/kg/day. The topical composition may include from 0.001 to 20% by weight for example 0.01 to 5%, of the active compound.

The novel compounds may be prepared by the Friedel-Crafts reaction (Gore in Olah's, Friedel-Crafts and Related Reactions, vol III, pp 1–381. Interscience, New York, 1964)

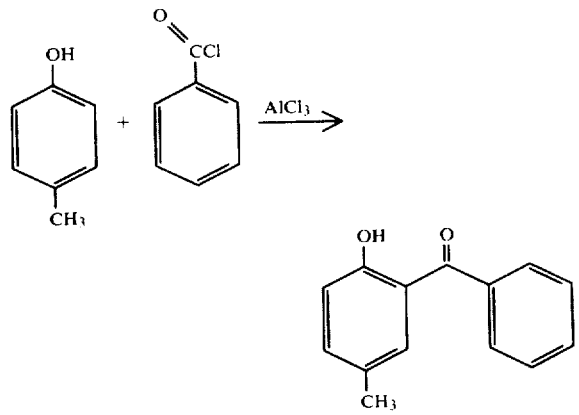

or via the Houben-Hoesch Reaction (Ruske in Olah's Friedel-Crafts and Related Reactions, vol III pp 383-497. Interscience, New York, 1964).

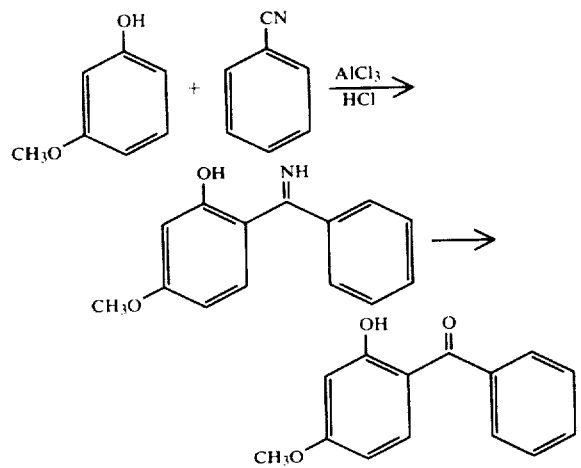

Inhibition of prostaglandin synthesis has been shown to be the major mode of action of non-steroidal anti-inflammatory drugs (Ferreira and Vane, 1974). A commonly used model system for examination of prostaglandin synthetase inhibition is the sheep vesicular gland microsomal preparation (Wallach and Daniels, 1971). Prostaglandin synthetase activity was determined by following oxygen tension in a closed reaction chamber using a Clark-type oxygen electrode. For each assay 2.9 ml of 0.1 M Tris HCl buffer, pH 8.0, 10 ul of 0.2 M phenol, and 50 ul of enzyme suspension (2.5 mg microsomal preparation) were added to the reaction chamber. Ten ul of inhibitor in ethanol was added 1 minute prior to initiation of the reaction. The reaction was initiated by addition of 10 ul of 3.6 mM arachidonate solution. The concentration of an inhibitor that reduced prostaglandin synthesis by 50% ($[I]_{50}$) was determined from plots of activity vs log concentration of inhibitor. Compounds with $[I]_{50}$ values of less than 10 uM were deemed useful in the treatment of inflammation. The compounds of this invention have $[I]_{50}$ values in the range of 1 to 10 uM, for example the $[I]_{50}$ of 2-hydroxybenzophenone was 3.8 uM.

The anti-inflammatory activity of these compounds is observed in various standard pharmacological tests, as for example carrageenan induced foot-pad edema in rats (Winter et. al. 1963), or the reverse passive arthus reaction in rabbits (Goldlust and Schreiber 1975).

EXAMPLES

EXAMPLE 1

Preparation of
2',3'-dichloro-2-hydroxy-5-methylbenzophenone 20.9 g of 2,3-dichlorobenzoyl chloride and 10.8 g, p-cresol are placed in a flask fitted with an air condenser and a calcium chloride tube. 13.3 g of aluminum chloride is added in small portions of about 2 grams. After each addition the mixture is warmed and shaken well to allow evolution of HCl. The mixture is then heated for 8 hours at 190° C. The crude product is treated with dilute HCl and distilled with steam. The distillate is extracted with ether and yields product on evaporation which is recrystalized.

2',6'-Dichloro-2-hydroxy-5-methylbenxophenone, 3'-chloro-2',5-dimethyl-2-hydroxybenzophenone, and 2-hydroxy-5-methyl-3'-trifluoromethylbenzophenone are synthesized similarily from p-cresol, aluminum chloride and 2,6-dichloro-, 3-chloro-, or 3-trifluoromethylbenzoyl chloride.

EXAMPLE 2

Preparation of
2',6'-dichloro-2-hydroxy-4-methoxy-benzophenone 20.9 g of 2,6-dichlorobenzoyl chloride and 12.4 g, m-methoxyphenol are placed in a flask fitted with an air condenser and a calcium chloride tube. 13.3 g of aluminum chloride is added in small portions of about 2 grams. After each addition the mixture is warmed and shaken well to allow evolution of HCl. The mixture is then heated for 8 hours at 190° C. The crude product is treated with dilute HCl and distilled with steam. The distillate is extracted with ether and yields product on evaporation which is recrystalized.

2',3'-Dichloro-2-hydroxy-4-methoxybenxophenone is synthesized similarily from m-methoxyphenol aluminum chloride and 2,3-dichlorobenzoyl chloride.

EXAMPLE 3

Preparation of 2-hydroxy-4-methoxy-3'-trifluoromethyl benzophenone 17.1 g of m-(trifluoromethyl)benzonitrile and 12.4 g of m-methoxyphenol are placed in a flask fitted with an air condenser and calcium chloride tube. 13.3 g of aluminum chloride is added in small portions of about 2 g. After each addition the mixture is warmed and shaken well so that evolution of HCl occurs. The mixture is then heated for 8 hours at 190° C. The imine is converted to the ketone by treatment with dilute HCl. The product is distilled with steam. The distillate is extracted with ether and yields crude product on evaporation. The product is recrystalized.

3'Chloro-2-hydroxy-4-methoxybenzophenone is prepared similarly from m-methoxyphenol, aluminum chloride and m-chlorobenzonitrile.

EXAMPLE 4

A mixture of 250 parts of 2-hydroxybenzophenone and 25 parts of lactose is granulated with suitable water, and to this is added 100 parts of maize starch. The mass is passed through a 16 mesh screen. The granules are dried at a temperature below 60° C. The dry granules are passed through a 16 mesh screen, and mixed with 3.8 parts of magnesium stearate. They are then compressed into tablets suitable for oral administration.

The 2-hydroxybenzophenone used in the foregoing examples may be replaced by 25, 100, or 500 parts of substituted hydroxybenzophenones of this invention to produce tablets suitable for oral administration as an anti-inflammatory, antipyretic and/or analgesic according to the method of this invention.

EXAMPLE 5

A mixture of 50 parts of 2-hydroxy-5-methyl-3'-trifluoromethybenzophenone, 3 parts of the calcium salt of lignin sulphonic acid, and 237 parts of water is ball-milled until the size of substantially all of the particles of benzophenone are less than 10 microns. The suspension is diluted with a solution containing 3 parts of sodium carboxymethylcellulose and 0.9 parts of the butyl ester of p-hydroxybenzoic acid in 300 parts of water. There is thus obtained an aqueous suspension suitable for oral administration for therapeutic purposes.

EXAMPLE 6

A mixture of 250 parts of 2',3'-dichloro-2-hydroxy-5-methylbenzophenone, 200 parts of maize starch and 30 parts of alginic acid is mixed with a sufficient quantity of a 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

EXAMPLE 7

A mixture of 500 parts 2-hydroxy-4-methoxybenzophenone, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

EXAMPLE 8

10,000 scored tablets for oral use, each containing 500 mg. of hydroxybenzophenone, are prepared from the following ingredients:

|  | Grams |
| --- | --- |
| 4'-chloro-2-hydroxybenzophenone | 5000 |
| Starch, U.S.P. | 350 |
| Talc, U.S.P. | 250 |
| Calcium stearate | 35 |

The powdered hydroxybenzophenone is granulated with a 4% w/v aqueous solution of methylcellulose U.S.P. (1500 cps.). To the dried granules is added a mixture of the remainder of the ingredients and the final mixture compressed into tablets of proper weight.

EXAMPLE 9

An oil/water ointment is prepared from the following ingredients:

|  | Grams |
| --- | --- |
| Calcium Citrate | 0.05 |
| Sodium Alginate | 3.0 |
| Methylparaben | 0.2 |
| Glycerin | 45.0 |
| 2-Hydroxybenzophenone | 1.0 |
| Distilled Water, sufficient, To make | 100.00 |

The calcium citrate and methylparaben are dissolved in the water. The 2-hydroxybenzophenone is dissolved in glycerin and mixed with sodium algenate to form a smooth paste. The aqueous mixture is added and stirred until a smooth, stiff preparation is obtained.

EXAMPLE 10

An hydrophilic petrolatum preparation is prepared from the following ingredients:

|  | Grams |
| --- | --- |
| 2-Hydroxy-4-methoxybenzophenone | 10 |
| Cholesterol | 30 |
| Stearyl Alcohol | 30 |
| White Wax | 80 |
| White Petrolatum, sufficient, To make | 1000 |

The 2-hydroxy-4-methoxybenzophenone, steayl alcohol, white wax and white petrolatum are melted on a steam bath, then the cholesterol is added and the mixture stirred until all components are completely dissolved. The mixture is removed from the bath and allowed to congeal.

What I claim is:

1. A method of treating inflammation or pain in mammals, which method comprises administering to the mammal a therapeutically effective amount of a compound of the formula:

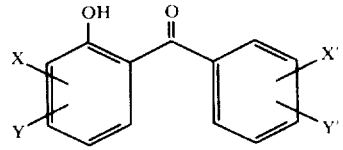

where X, Y, X', and Y' are hydrogen, halogen, $C_1$-$C_8$ alkyl, $C_1$-$C_8$ haloalkyl, $C_1$-$C_8$ alkoxy or combinations thereof and the nontoxic pharmaceutically acceptable salts thereof.

2. The method of claim 1 where X is an alkoxy radical, and Y, X', and Y' are hydrogen.

3. The method of claim 3 where X' is halogen.

4. The method of claim 3 where X' is trihalomethyl.

5. The method of claim 3 where X' and Y' are halogen.

6. The method of claim 3 where X' is halogen, and Y' is a loweralkyl.

7. The method of claim 1 where X is hydrogen, Y is methyl, X' is methyl, and Y' is hydrogen.

8. The method of claim 7 where X' is halogen.

9. The method of claim 7 where X' is trihalomethyl.

10. The method of claim 7 where X' and Y' are halogen.

11. The method of claim 7 where X' is halogen, and Y' is lower alkyl.

12. The method of claim 1 wherein the compound is selected from the group consisting of:
2-hydroxybenzophenone
2-hydroxy-4-methoxybenzophenone
4'-chloro-2-hydroxy-4-methoxybenzophenone
2',3'-dichloro-2-hydroxy-4-methoxybenzophenone
2',6'-dichloro-2-hydroxy-4-methoxybenzophenone
3'-chloro-2-hydroxy-4-methoxy-2'-methylbenzophenone
2-hydroxy-4-methoxy-3'-trifluoromethylbenzophenone
2-hydroxy-4'-methyl-4-methoxy-benzophenone
2-hydroxy-4-octyloxybenzophenone
5-chloro-2-hydroxy-4-methylbenzophenone
5-chloro-2-hydroxybenzophenone
4'-chloro-2-hydroxybenzophenone
2-hydroxy-5-methylbenzophenone
2',3'-dichloro-2-hydroxy-5-methylbenzophenone
2',6'-dichloro-2-hydroxy-5-methylbenzophenone
3'-chloro-2',5-dimethyl-2-hydroxybenzophenone
2-hydroxy-5-methyl-3'-trifluoromethylbenzophenone 13. The method of claim 1 which comprises applying the compound in a topical preparation to or about the area of inflammation or pain.

14. A method of claim 13 where the preparation comprises from about 0.001 to 5 percent by weight of the compound as an active ingredient.

15. The method of claim 1 which comprises oral administration of the compound.

16. The method of claim 1 which comprises parentral administration of the compound.

17. The method of claim 1 wherein X' and Y' are chloro.

18. The method of claim 1 wherein X' is trifluoromethyl.

19. The method of claim 1 wherein X' is chloro and Y' is methyl.

20. The method of claim 1 wherein X is methoxy.

* * * * *